US010926033B2

(12) United States Patent
Masumoto

(10) Patent No.: US 10,926,033 B2
(45) Date of Patent: Feb. 23, 2021

(54) INJECTOR

(71) Applicant: DAICEL CORPORATION, Osaka (JP)

(72) Inventor: Takaya Masumoto, Hyogo (JP)

(73) Assignee: Daicel Corporation, Osaka (JP)

( * ) Notice: Subject to any disclaimer, the term of this patent is extended or adjusted under 35 U.S.C. 154(b) by 124 days.

(21) Appl. No.: 16/221,339

(22) Filed: Dec. 14, 2018

(65) Prior Publication Data

US 2019/0117894 A1    Apr. 25, 2019

Related U.S. Application Data

(63) Continuation of application No. PCT/JP2017/021993, filed on Jun. 14, 2017.

(30) Foreign Application Priority Data

Jun. 17, 2016    (JP) .............................. JP2016-120778

(51) Int. Cl.
*A61M 5/20* (2006.01)
*F42B 3/00* (2006.01)
(Continued)

(52) U.S. Cl.
CPC ............ *A61M 5/2046* (2013.01); *A61M 5/30* (2013.01); *F42B 3/006* (2013.01); *F42B 12/54* (2013.01); *F15B 15/19* (2013.01); *F42B 3/04* (2013.01)

(58) Field of Classification Search
CPC ....... A61M 5/2046; A61M 5/30; F42B 3/006; F42B 3/04
See application file for complete search history.

(56) References Cited

U.S. PATENT DOCUMENTS 2,575,071 A * 11/1951 Rockwell ................ F15B 15/19
                                                                    60/632
3,669,111 A *  6/1972 Dubner ............... A61M 5/3148
                                                                   604/229
(Continued)

FOREIGN PATENT DOCUMENTS

JP    2004-532049 A    10/2004
JP    2005-523679 A     8/2005
(Continued)

OTHER PUBLICATIONS

International Search Report and Written Opinion dated Aug. 22, 2017 in International Application No. PCT/JP2017/021993.
(Continued)

*Primary Examiner* — Laura A Bouchelle
(74) *Attorney, Agent, or Firm* — Knobbe Martens Olson & Bear LLP

(57) ABSTRACT

An injector can include an ignition device having a partition member which forms a first space to store a gunpowder and which is formed of a prescribed rigid material such that the partition member is breached based on a rise in pressure of the first space when the gunpowder is burned. The injector can also include a case including a base section fixed on a side of the ignition device. The case can be arranged in a space inside the injector main body so as to cover the ignition device. The case can define a second space with the partition member of the ignition device and encapsulate, inside the second space, a combustion product of the gunpowder. When the gunpowder burns in the ignition device and pressure inside the second space rises, a part of the case extends so as to approach a prescribed end section.

12 Claims, 5 Drawing Sheets

(51) Int. Cl.
*F42B 12/54* (2006.01)
*A61M 5/30* (2006.01)
*F15B 15/19* (2006.01)
*F42B 3/04* (2006.01)

(56) References Cited

U.S. PATENT DOCUMENTS

| | | | |
|---|---|---|---|
| 3,802,430 A * | 4/1974 | Schwebel | A61M 5/30 604/69 |
| 7,063,019 B2 | 6/2006 | Parks et al. | |
| 2004/0015125 A1 | 1/2004 | Alexandre et al. | |
| 2016/0129190 A1 | 5/2016 | Haitsuka | |
| 2017/0343021 A1 | 11/2017 | Yamada et al. | |
| 2018/0328388 A1 | 11/2018 | Yamada et al. | |

FOREIGN PATENT DOCUMENTS

| | | |
|---|---|---|
| JP | 2007-525192 A | 9/2007 |
| JP | 2008-508881 A | 3/2008 |
| JP | 2008-206477 A | 9/2008 |
| JP | 2010-503616 A | 2/2010 |
| JP | 2014-239819 A | 12/2014 |
| JP | 2016-151318 A | 8/2016 |
| WO | WO 00/50107 | 8/2000 |
| WO | WO 2003/004620 A2 | 1/2003 |
| WO | WO 2005/019453 A2 | 3/2005 |
| WO | WO 2006/015373 A2 | 2/2006 |
| WO | WO 2008/047243 A2 | 4/2008 |

OTHER PUBLICATIONS

Extended European Search Report dated Nov. 5, 2019 in European Application No. 17813358.3, in 8 pages.

* cited by examiner

INJECTOR

INCORPORATION BY REFERENCE TO ANY PRIORITY APPLICATIONS

This application is a continuation application, and claims the benefit under 35 U.S.C. §§ 120 and 365 of PCT Application No. PCT/JP2017/021993, filed Jun. 14, 2017, which is hereby incorporated by reference. PCT/JP2017/021993 also claimed priority to Japanese Patent Application No. 2016-120778, filed Jun. 17, 2016, the entire contents of which are incorporated by reference.

BACKGROUND

Field

The described technology generally relates to an injector for injecting an injection objective substance into an injection target region of a target object.

Description of the Related Technology

An ejection of an injection solution in an injector is realized by pressurizing the injection solution regardless of whether or not a needle is present. For example, with a needle-free injector which performs an injection without involving a needle, gunpowder may be used as a pressurization source of the injection (for example, refer to JP 2004-532049). With the needle-free injector described in 2004-532049, a detonator and a pyrotechnic charge are provided, and when a firing hammer pierces the detonator and the detonator ignites, heat energy of the ignition is transferred to the pyrotechnic charge. Subsequently, the pyrotechnic charge burns and an injection solution is pressurized. As such a pyrotechnic charge, a single nitrocellulose-based gunpowder is used.

In addition, U.S. Pat. No. 7,063,019 discloses an igniter which utilizes combustion energy of a gunpowder. With the disclosed technique, a circumferential wall portion of a cup forming an outer shell of the igniter is formed in a bellows shape, and prior to combustion of a gunpowder inside the igniter, the bellows portion is contracted in an axial direction of the cup. When the ignition charge burns, the bellows portion is extended as pressure inside the igniter rises, thereby propelling a position of a tip portion of the cup in the axial direction of the cup. PTL 2 also discloses a mode in which such a propelling action of the cup tip portion is utilized as an output section of an actuator.

SUMMARY

When combustion energy of a gunpowder is used as a power source for pressurization, effects of combustion products such as a combustion gas and combustion residue which are generated by the combustion must be taken into consideration. For example, when a gunpowder is used as a pressurization source of an injection solution in an injector, a situation where a combustion product becomes mixed with an injection objective substance such as an injection solution that is a pressurization target is undesirable from a hygiene perspective.

On the other hand, with an igniter such as that described as a conventional technique, an injection solution can be pressurized by utilizing the propelling action of the cup tip portion while encapsulating a combustion product created by the combustion of the gunpowder in the cup. However, when the bellows portion provided in the cup of the igniter extends in accordance with pressure in an internal space attributable to combustion of the ignition charge, an increase in a capacity of the internal space of the igniter as the bellows portion extends may possibly affect, and slow down, a combustion rate of the gunpowder. Therefore, even if the igniter according to the conventional technique is adopted as a pressurization source of an injector, since a pressure rise of the internal space of the igniter slows down and an output thereof declines, it may not be possible to pressurize an injection solution in a desired manner.

Therefore, in consideration of the problem described above, an object of the present invention is to, in an injector which ejects an injection objective substance such as an injection solution by means of gunpowder combustion, suppress effects of a combustion product generated by the gunpowder combustion on the injection objective substance and perform pressurization of the injection objective substance in a preferable manner.

In order to solve the problem described above, the present invention adopts a configuration in which a gunpowder inside an ignition device is stored in a first space formed by a partition member that is breached by a pressure rise and, on the other hand, a case storing the ignition device is not breached by a pressure rise in a second space inside the case and a combustion product of the gunpowder is continuously encapsulated inside the second space. Additionally, a configuration is adopted in which the case is provided with an extending section in order to cause a part of the case to be propelled by a pressure rise inside the second space and function as an output section of an actuator.

Specifically, the present invention provides an injector for injecting an injection objective substance into an injection target region, the injector including: an injector main body having a through-hole formed in an axial direction; a piston section arranged so as to be slidable inside the through-hole; a syringe section arranged on a tip side of the injector main body, the syringe section having a storage chamber which is capable of storing the injection objective substance, a plunger which pressurizes the injection objective substance inside the storage chamber as the piston section slides, and a nozzle section which includes a flow path through which the injection objective substance that is present inside the storage chamber and has been pressurized by the plunger flows and which ejects the injection objective substance from an ejection port formed at a tip of the flow path; an ignition device having a partition member which forms a first space to store a gunpowder and which is formed by a prescribed rigid material such that the partition member is breached due to a rise in pressure of the first space when the gunpowder is burned; and a case of which a base section is fixed on a side of the ignition device and which is arranged in a space inside the injector main body so as to cover the ignition device, the case defining a second space with the partition member of the ignition device and encapsulating, inside the second space, a combustion product generated by combustion of the gunpowder in the ignition device. In addition, the case includes: an extending section which, due to a rise in pressure inside the second space by gunpowder combustion in the ignition device, extends in an approach direction in which a part of the case approaches a prescribed end section of the piston on a side opposite to an end section opposing the plunger; and a pressing section which is provided in the part of the case and which presses the prescribed end section of the piston as the extending section extends.

In the injector according to the present invention, energy created by gunpowder combustion in the ignition device is transferred to the piston section to cause the piston section to slide inside the through-hole. In addition, as pressure is applied via the plunger to an injection objective substance stored in the storage chamber of the syringe section due to sliding of the piston section, the injection objective substance is ejected to the outside of the injector from the ejection port. It should be noted that the transfer of energy to the piston section by the combustion of gunpowder is performed via the case as will be described later or, in other words, sliding of the piston section is realized as the case operates as an actuator that uses the combustion energy as a driving source.

In addition, the injection objective substance includes a component expected to be efficacious inside the injection target region, and when ejection by ejection energy is possible, a stored state of the injection objective substance inside the injector and a specific physical form of the injection objective substance such as a liquid, a gel-like fluid, a powder, or a granular solid need not matter. Furthermore, the injection objective substance may include a component to be delivered to the injection target region of a living organism that is a target object, and the component may be present in a dissolved state inside the injection objective substance or may be simply present in a mixed state instead of being dissolved. Examples of the component to be delivered include a vaccine for antibody enhancement, a protein for cosmetic purposes, and cultured cells for hair regrowth, in which case the injection objective substance is formed by having a liquid or a gel-like fluid contain the component so as to enable the component to be ejected. In addition, the injector may be of a type which supplies the injection objective substance to the injection target region via a needle or a type which supplies the injection objective substance to the injection target region without involving a needle. In the injector according to the present invention, specific components of the gunpowder are not limited to certain components.

When the gunpowder burns in the ignition device configured as described above, a combustion product thereof is diffused in the first space formed by the partition member and pressure inside the first space rises. In this case, the partition member is formed by a prescribed rigid material so as to be breached when pressure of the first space rises and, therefore, the first space substantially remains undeformed until breached. Therefore, after the gunpowder starts burning, the pressure inside the first space can rise rapidly. As the prescribed rigid material, a resin material can be preferably adopted. Subsequently, when the partition member is breached by the pressure inside the first space, the combustion product of the gunpowder is to be diffused in the second space. In this case, since the pressure inside the first space rises rapidly due to the partition member as described above, the combustion of the gunpowder proceeds rapidly without slowing down along the way. This contributes to preferably adjusting a timing of pressurization of the injection objective substance.

In this case, unlike the partition member of the ignition device, the case forming the second space is not breached even when pressure of the second space rises and the combustion product of the gunpowder is encapsulated inside the second space. In addition, when the pressure of the second space rises, the extending section included in the case extends, the part of the case approaches the prescribed end section of the piston section, and the prescribed end section is pressed by the pressing section provided in the part of the case. Due to a deformation of such the case, energy created by the combustion of the gunpowder is to be transferred to the piston section. In other words, due to the case having the extending section and the pressing section, the case is to operate as an actuator which uses energy created by the combustion of the gunpowder as a driving source.

As described above, in the injector according to the present invention, since the gunpowder is burned inside the first space formed by the partition member, the pressure of the first space can be readily and rapidly increased. In addition, since combustion of the gunpowder causes the extending section to extend and causes the pressing section to press the piston section, preferable pressurization of the injection objective substance is realized. Furthermore, in the pressurization process, the combustion product of the gunpowder is kept encapsulated in the second space. Therefore, an effect of combustion residue and the like can be avoided and, in particular, the combustion residue and the like can be prevented from coming into contact with the injection objective substance. In addition, since the encapsulation in the second space is maintained, noise (combustion noise) generated by the combustion of the gunpowder is less likely to leak outside the space, thereby increasing convenience of a user when using the injector.

In the injector described above, a gas generating agent which generates a prescribed gas by combustion may be stored inside the second space, and the extending section may be configured such that the part of the case extends in the approach direction as pressure inside the second space rises due to gunpowder combustion in the ignition device and combustion of the gas generating agent. In such a configuration, when the partition member is breached by pressure inside the first space created by the combustion of gunpowder, the gas generating agent stored in the second space is exposed to and receives heat from the combustion product of the gunpowder and, consequently, combustion of the gas generating agent starts. In this case, since the pressure inside the first space rises rapidly due to the partition member, the combustion of the gas generating agent is also started rapidly or, in other words, a timing of combustion of the gas generating agent via the gunpowder can be more readily adjusted to a desired timing. This contributes to preferably adjusting a timing of pressurization of the injection objective substance.

Subsequently, when the gas generating agent starts to burn, the generated prescribed gas diffuses in the second space, a rise in the pressure inside the second space causes the extending section to extend and causes the prescribed end section to be pressed, thereby causing energy created by the combustion of the gunpowder and the gas generating agent to be transferred to the piston section. Even in this configuration, the combustion product of the gunpowder and the prescribed gas created by the gas generating agent are encapsulated inside the second space. Therefore, the combustion residue and the like can be prevented from coming into contact with the injection objective substance and noise (combustion noise) created by the combustion of the gunpowder and the gas generating agent can be suppressed. It should be noted that, in the injector according to the present invention, specific components of the gas generating agent are not limited to certain components.

In this case, in the injector described above, the extending section may be formed in a side wall section of the case opposing an inner wall surface that extends in an axial direction of the injector main body so as to be folded in a bellows shape in a state prior to gunpowder combustion in the ignition device and configured so as to extend in the axial direction due to gunpowder combustion in the ignition device. By forming the extending section in a bellows shape in this manner, the folded bellows portion is expanded due to a pressure rise of the second space and the pressing section provided in the part of the case can be caused to approach and be propelled toward the prescribed end surface of the piston section.

In addition, in the injector described above, the part of the case may be an end surface on a tip side of the case, and an area of the tip-side end surface of the case may be formed larger than an end surface area of the prescribed end section of the piston section. According to such a configuration, when the extending section is extended, the pressing section provided on the end surface of the case more reliably comes into contact with the prescribed end section of the piston section and can more reliably transfer combustion energy of the gunpowder and the like to the piston section.

It should be noted that, in a configuration in which the extension of the extending section causes the pressing section to press the prescribed end section of the piston section as described above, the combustion of the gunpowder and the gas generating agent causes relatively large pressure to be applied to the part of the case where the pressing section is provided. In consideration thereof, a thickness in the part of the case may be formed so as to be thicker than a thickness of the case in portions other than the part so as to increase strength of an area subjected to the pressure. In addition, as an alternative method of reinforcing the area, a reinforcing plate having a prescribed thickness may be provided inside or outside the case in the part of the case. The prescribed thickness of the reinforcing plate is set in consideration of the pressure applied to the part of the case to a sufficient thickness that prevents the case from being breached when pressing by the pressing section is being performed.

In this case, in the injector described above, the case may be arranged inside the injector main body so that the pressing section comes into contact with the prescribed end section of the piston section in a state prior to gunpowder combustion in the ignition device. Due to such an arrangement, when the pressure of the second space starts to rise, the pressure can be promptly transferred to the piston section.

In addition, the injector described above may be configured such that, in a state where the extending section is extended to the maximum due to gunpowder combustion in the ignition device, a prescribed gap is present between the part of the case and a prescribed inner wall surface forming an internal space of the injector main body, the inner wall surface being in a vicinity of an end section of the through-hole and opposing the part of the case. According to such a configuration, when the extending section is extended to the maximum, a state where the part of the case comes into contact with the prescribed inner wall surface can be avoided. As a result, the part of the case can be prevented from being subject to a relatively large impact from the prescribed inner wall surface at the time of the maximum extension, thereby contributing to maintaining an encapsulated state of a combustion product and the like by the second space. In addition, as an alternative method, in the injector described above, a cushioning member may be provided on a prescribed inner wall surface which forms an internal space of the injector main body, the inner wall surface being in a vicinity of an end surface of the through-hole and opposing the part of the case, in which case when the extending section is extended by a gunpowder combustion in the ignition device, the extending section comes into contact with the cushioning member and the extension of the extending section is stopped. By causing the part of the case to come into contact with the prescribed inner wall surface via the cushioning member in this manner, an impact upon the contact can be reduced.

According to the present invention, in an injector which ejects an injection objective substance such as an injection solution by means of gunpowder combustion, effects of a combustion product generated by the gunpowder combustion on the injection objective substance can be suppressed and pressurization of the injection objective substance can be performed in a preferable manner.

DETAILED DESCRIPTION

Hereinafter, a needle-free injector 1 (hereinafter, simply referred to as an "injector 1") without a needle will be described as an example of an injector according to an embodiment of the present invention with reference to the drawings. It is to be understood that configurations of the embodiment described below are illustrative and that the present invention is not limited to the configurations of the embodiment described below.

First Embodiment

Figure 1A:
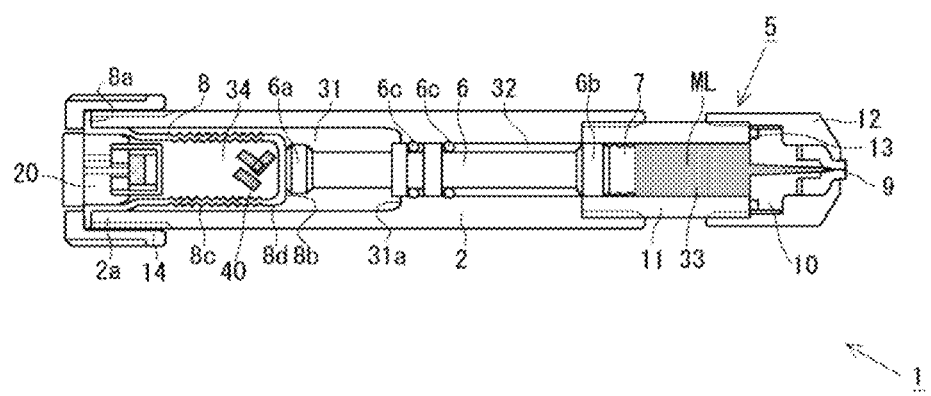
FIGS. 1A, 1B and 1C are diagrams showing a schematic configuration of an injector according to a first embodiment of the present invention.
Figure 1B:
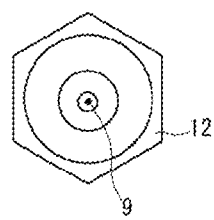

FIG. 1A is a sectional view of the injector 1 and FIG. 1B is a diagram of the injector 1 as viewed from a side of a nozzle section 9 which ejects an injection solution. It should be noted that, in the subsequent description of the present specification, injection objective substances to be injected into an injection target region of a target object by the injector 1 will be collectively referred to as an "injection solution". However, the term is not intended to limit contents or forms of the substances to be injected. In the injection objective substance, a component to be delivered to a skin structure that is an example of the injection target region may be either dissolved or undissolved and, at the same time, a specific form of the injection objective substance need not matter as long as the injection objective substance can be ejected to the skin structure from the nozzle section 9 by pressurization and various forms such as a liquid, a gel-like form, and a powder-like form can be adopted.

Figure 2A:
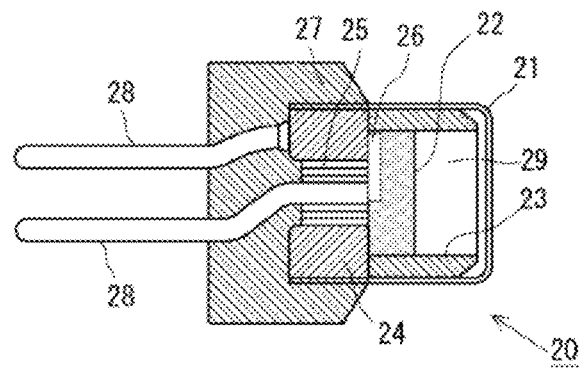
FIGS. 2A and 2B are diagrams showing a schematic configuration of an initiator (an ignition device) mounted to the injector shown in FIGS. 1A-1C.
Figure 2B:
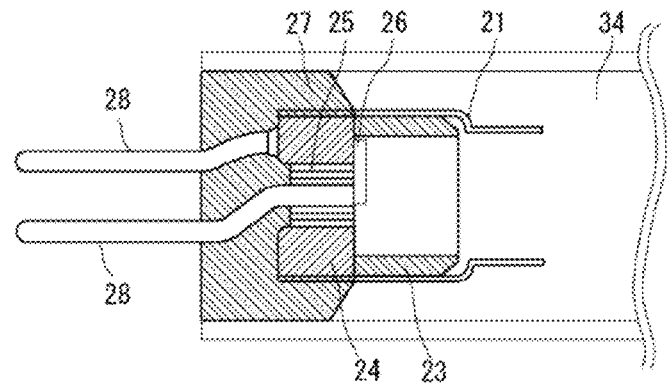

In this case, the injector 1 has an injector main body 2, and a syringe section 5 is arranged on a tip side of the injector main body 2. In addition, an initiator 20 that is an ignition device to be described later is arranged at another end section of the injector main body 2. An example of the initiator 20 will be described with reference to FIGS. 2A and 2B. FIG. 2A represents a state (hereinafter, referred to as a "state before ignition") of the initiator 20 prior to performing gunpowder combustion, and FIG. 2B represents a state of the initiator 20 when the gunpowder combustion has ended.

In this case, the initiator 20 is an electric ignition device, and a cup 21 (corresponding to the partition member according to embodiments of the present invention) of which a surface is covered by an insulating cover made of resin defines, inside the cup 21, a space 29 (corresponding to the first space according to embodiments of the present invention) for arranging a gunpowder 22. In addition, a metal header 24 is arranged in the space, and a cylindrical charge holder 23 is provided on an upper surface of the metal header 24. The gunpowder 22 is held by the charge holder 23. A bridge wire 26 which electrically connects one conductive pin 28 with the metal header 24 is arranged in a bottom section of the gunpowder 22. Two conductive pins 28 are fixed to the metal header 24 via an insulator 25 so as to be insulated from each other when voltage is not being applied. Furthermore, an opening of the cup 21 through which the two conductive pins 28 supported by the insulator 25 extend is protected by a resin collar 27 in a state where insulation between the conductive pin 28 is favorably maintained.

In the initiator 20 configured as described above, when voltage is applied between the two conductive pins 28 by an external power source, a current flows through the bridge wire 26 and, accordingly, the gunpowder 22 burns. In this case, in an initial stage of combustion of the gunpowder 22 sealed in the space 29 that is an enclosed space formed by the cup 21 and the resin collar 27, the gunpowder 22 burns while the sealed state of the space 29 is maintained. The cup 21 is formed by a resin material and has certain rigidity and strength. Therefore, while a shape of the cup 21 is more or less maintained until pressure of the space 29 reaches prescribed pressure, once the pressure exceeds the prescribed pressure, a bottom surface section (an area opposing an opening of the charge holder 23) is breached as shown in FIG. 2B. In other words, the bottom surface section of the cup 21 opens so as to communicate the space 29 and a combustion chamber 34 (to be described later) with each other. At this point, a combustion product created by the combustion of the gunpowder 22 is to be ejected into the combustion chamber 34 from the opening of the cup 21 created by the breach described above.

Favorable examples of the gunpowder 22 used in the injector 1 include gunpowder (ZPP) containing zirconium and potassium perchlorate, gunpowder (THPP) containing titanium hydride and potassium perchlorate, gunpowder (TiPP) containing titanium and potassium perchlorate, gunpowder (APP) containing aluminum and potassium perchlorate, gunpowder (ABO) containing aluminum and bismuth oxide, gunpowder (AMO) containing aluminum and molybdenum oxide, gunpowder (ACO) containing aluminum and copper oxide, and gunpowder (AFO) containing aluminum and iron oxide, and gunpowder consisting of a combination of a plurality of these gunpowders. These gunpowders exhibit characteristics in that, while high-temperature and high-pressure plasma is generated during combustion immediately after ignition, generated pressure drops abruptly once the temperature drops to normal temperature and a combustive organism condenses since the gunpowders do not contain a gaseous component. It should be noted that gunpowders other than the above may be used as an ignition charge.

Returning to FIGS. 1A-1C, in the injector 1, an initiator cap 14 is formed with a flange-like cross section so as to be hooked on an outer surface of the initiator 20, and the initiator cap 14 is fixed to the injector main body 2 by screws. Accordingly, the initiator 20 is fixed to the injector main body 2 by the initiator cap 14, and the initiator 20 itself can be prevented from falling off of the injector main body 2 due to pressure created during ignition in the initiator 20.

In addition, a space 31 that is an internal space extending in an axial direction of the injector main body 2 is formed on a side of the initiator 20 inside the injector main body 2, and a through-hole 32 that is an internal space similarly extending in the axial direction of the injector main body 2 is formed on a side of the syringe section 5 inside the injector main body 2. The space 31 and the through-hole 32 are also an internal space that is continuously arranged inside the injector main body 2.

Furthermore, the syringe section 5 provided on a tip side of the injector main body 2 has a syringe section main body 11 having, therein, a storage chamber 33 which stores an injection solution ML, the nozzle section 9 in which a flow path through which the injection solution flows is formed, and a nozzle holder 10 provided with the nozzle section 9. The nozzle holder 10 is attached to the syringe section main body 11 by a holder cap 12 so as to sandwich a gasket 13. In addition, the syringe section main body 11 is mounted by screwing to an end section of the injector main body 2 and, in the mounted state, the through-hole 32 inside the injector main body 2 and the storage chamber 33 inside the syringe section main body 11 become a continuous space. In the mounted state, the injection solution ML is liquid-tightly stored in the storage chamber 33 by a plunger 7, and the plunger 7 is exposed to a side of the through-hole 32. In this case, the plunger 7 is arranged so as to be slidable inside the storage chamber 33 and, due to sliding of the plunger 7, the injection solution ML is pressurized and ejection of the injection solution from the nozzle section 9 is performed. Furthermore, the plunger 7 is formed by a rubber member of which a surface is thinly coated by silicone oil so that the plunger 7 can smoothly slide inside the storage chamber 33.

Figure 1C:
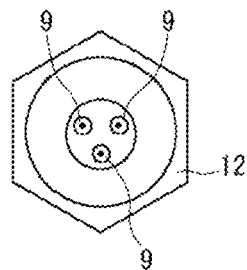

It should be noted that, in the nozzle holder 10, a single nozzle section 9 may be formed (refer to FIG. 1B) or a plurality of nozzle sections 9 may be formed (refer to FIG. 1C. When a plurality of nozzle sections are formed, a flow path corresponding to each nozzle section is formed so that the released injection solution ML is fed into each nozzle as uniformly as possible. In addition, when a plurality of nozzle sections 9 are formed, as shown in FIG. 1C, the respective nozzle sections are favorably arranged at equal intervals around a central axis of the injector 1. Furthermore, a flow path diameter of the nozzle section 9 is configured to be smaller than an inner diameter of the through-hole 32. Accordingly, ejection pressure of the injection solution upon ejection can be preferably raised.

Next, a piston 6 made of metal is arranged in the through-hole 32 inside the injector main body 2 and the piston 6 is held so as to be slidable inside the through-hole 32. The piston 6 is formed in roughly a shape of a shaft extending along an axial direction of the through-hole 32, and has an end section (hereinafter, referred to as "first end section") 6a on a side of the space 31 and an end section (hereinafter, referred to as "second end section") 6b on a side of the syringe section 5 or, in other words, in contact with the plunger 7 arranged in the syringe section 5, and an O ring 6c is arranged around the piston 6 so that the piston 6 can smoothly slide inside the through-hole 32.

An extending case 8 that is extended toward the first end section 6a of the piston 6 is fixed by a flange section 8a thereof to an end surface of an end section 2a of the injector main body 2 on a side of the initiator 20, and the extending case 8 is arranged in the space 31 inside the injector main body 2 so as to cover the cup 21 of the initiator 20. In addition, the extending case 8 and an outer surface of the cup 21 of the initiator 20 form a combustion chamber 34 (corresponding to the second space according to embodiments of the present invention) which is an enclosed space. Furthermore, a gas generating agent 40 which generates a prescribed gas by combustion is arranged inside the combustion chamber 34. Examples of the gas generating agent 40 include a single-base smokeless powder consisting of 98 percent by mass of nitrocellulose, 0.8 percent by mass of diphenylamine, and 1.2 percent by mass of potassium sulfate. Furthermore, various gas generating agents used in an airbag gas generator or a seat-belt pretensioner gas generator can also be used.

The gas generating agent 40 burns as a combustion product of the combustion of the gunpowder 22 in the initiator 20 flows into the combustion chamber 34 from the opening of the cup 21 and the gas generating agent 40 is exposed to the combustion product, thereby generating the prescribed gas. It should be noted that the extending case 8 has sufficient strength to prevent the extending case 8 from being breached even by pressure inside the combustion chamber 34 created by the gas generating agent 40. Therefore, a state where the combustion product by the gunpowder 22 and the prescribed gas by the gas generating agent 40 are encapsulated inside the extending case 8 is maintained. With the gas generating agent 40, since the prescribed gas generated during combustion contains a gas component even at normal temperature, a drop rate of generated pressure is low. Furthermore, although a combustion completion time of the gas generating agent 40 during combustion is extremely long as compared to the gunpowder 22 described earlier, by adjusting dimensions or a size, a shape, and particularly a surface profile of the gas generating agent 40 when arranging the gas generating agent 40 inside the combustion chamber 34, the combustion completion time of the gas generating agent 40 can be changed. Adjusting an amount, a shape, or an arrangement of the gas generating agent 40 as described above enables generated pressure inside the combustion chamber 34 to be appropriately adjusted.

In addition, the extending case 8 has a roughly hollow columnar shape, and a bottom section (corresponding to the pressing section according to embodiments of the present invention, and hereinafter referred to as a "pressing bottom section") 8b of the extending case 8 on a side of the piston 6 is arranged inside the injector main body 2 in the state before ignition of the initiator 20 and in a state of being in contact with the first end section 6a of the piston 6. Furthermore, an inner wall surface of the injector main body 2 or, in other words, a side wall section of the extending case 8 opposing an inner wall surface of the space 31 is provided with a bellows section 8c (corresponding to the extending section according to embodiments of the present invention) which is extended toward the first end section 6a of the piston 6 by a pressure rise in the combustion chamber 34 attributable to a combustion product ejected from the opening of the cup 21 during combustion of the gunpowder 22 and to the prescribed gas generated from the gas generating agent 40 is burned by the combustion product. In addition, in the state before ignition, the bellows section 8c is arranged in folded state where the bellows section 8c is extensible toward the first end section 6a of the piston 6. An operation of the extending case 8 due to gunpowder combustion in the initiator 20 will be described later. Furthermore, a portion in the side wall section of the extending case 8 where the bellows section 8c is not provided or, in other words, a portion that does not extend will be referred as a non-extending section 8d.

In the injector 1 configured as described above, when the gunpowder 22 burns in the initiator 20, a combustion product is generated and pressure inside the initiator 20 rises. Subsequently, when the pressure reaches the prescribed pressure described earlier, the bottom surface section of the cup 21 is breached and the combustion product is released into the combustion chamber 34 formed between the extending case 8 and the cup 21 and, at the same time, the gas generating agent 40 exposed to the combustion product burns and prescribed gas is generated. Since the combustion product and the prescribed gas are encapsulated in the combustion chamber 34, pressure inside the combustion chamber 34 rises with the generation of the prescribed gas. Accordingly, as the bellows section 8c extends, the pressing bottom section 8b presses the first end section 6a of the piston 6. As a result, pressure energy of the combustion chamber 34 is transferred to the piston 6, thereby pressurizing the injection solution inside the storage chamber 33. In this case, in the initiator 20, since the pressure rise inside the space 29 is not inhibited by an expansion of capacity of the space in which gunpowder combustion takes place as was the case in conventional art until the cup 21 is breached, the cup 21 does not significantly deform and the combustion product remains inside the space 29, thereby enabling the pressure inside the initiator 20 to promptly rise to prescribed pressure. This means that, in the gas generating agent 40 of which combustion is triggered by the combustion product, a combustion timing can be appropriately adjusted. In other words, by promptly raising the pressure inside the initiator 20, a timing at which the combustion product is supplied to the gas generating agent 40 by way of breaching the bottom surface section of the cup 21 can be adjusted to a desired timing suitable for ejection of the injection solution to the injection target region.

Figure 3:
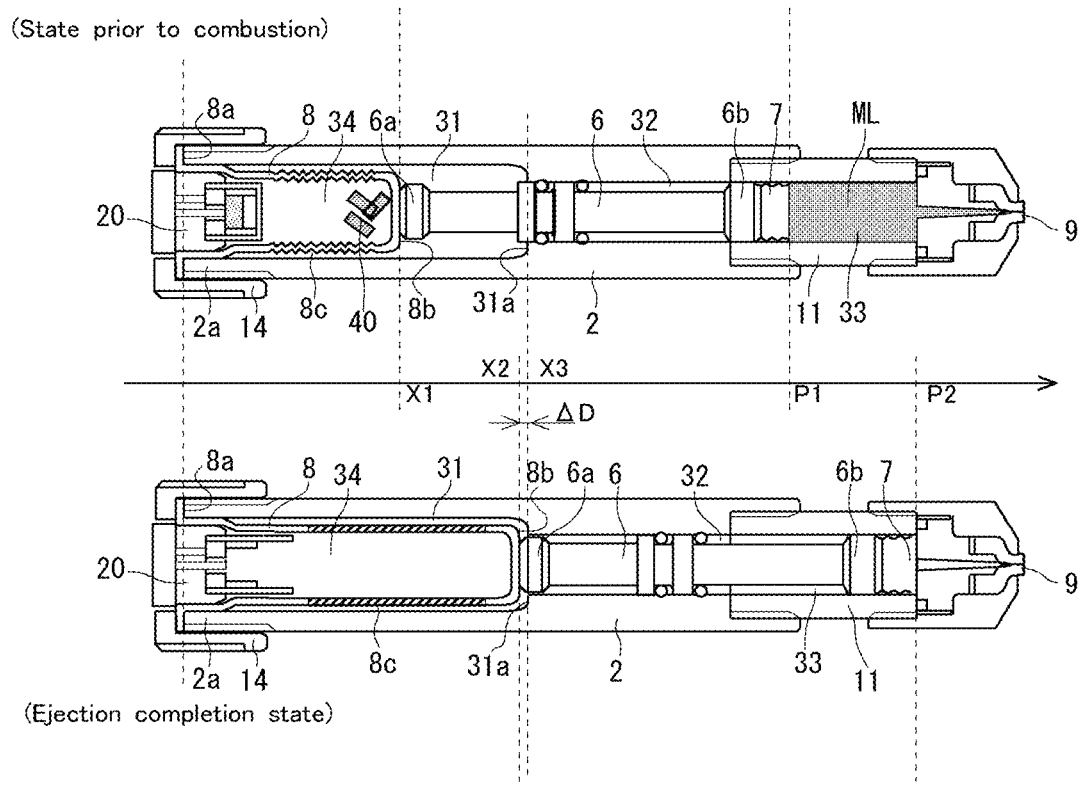
FIG. 3 is a diagram showing a comparison between a state prior to gunpowder combustion and a state after combustion (an ejection completion state) in the initiator in the injector shown in FIGS. 1A-1C.

A state where ejection of the injection solution is performed which is triggered by the combustion of the gunpowder 22 in the initiator 20 or, in other words, an ejection state of the injection solution in the injector 1 which is executed by an extending operation of the extending case 8 will be described with reference to FIG. 3. In FIG. 3, an upper half shows a configuration of the injector 1 in a state prior to ignition and a lower half shows a configuration of the injector 1 in a state where ejection of the injection solution by combustion of the gunpowder 22 has been completed (hereinafter, an "ejection completion state"). In a comparison between the state prior to ignition and the ejection completion state shown in FIG. 3, both states are represented side by side in the axial direction of the injector 1 with positions aligned at a surface fixed to the injector main body 2 in the flange section 8a of the extending case 8.

Furthermore, in a state prior to combustion, a position of the pressing bottom section 8b of the extending case 8 is represented by X1. In addition, a position of the plunger 7 at this point is represented by P1. In this state, when the gunpowder 22 burns and the cup 21 is breached as described above, the pressure inside the combustion chamber 34 rises as the combustion product diffuses into the combustion chamber 34 and the gas generating agent 40 burns. As described earlier, the bellows section 8c of the extending case 8 is arranged in a folded state where the bellows section 8c is extensible toward the first end section 6a of the piston 6. Due to a pressure rise inside the combustion chamber 34, the bellows section 8c is extended toward the first end section 6a of the piston 6. At this point, the pressing bottom section 8b presses the first end section 6a of the piston 6. Therefore, an end surface of the first end section 6a of the piston 6 with which the pressing bottom section 8b comes into contact is an end surface which receives combustion energy of the gunpowder 22 and the gas generating agent 40. It should be noted that an area of the pressing bottom section 8b is designed larger than an area of the first end section 6a. Therefore, when the bellows section 8c is extended, the pressing bottom section 8b more reliably comes into contact with the first end section 6a of the piston 6 and the combustion energy described above can be transferred to the piston 6.

Pressing by the pressing bottom section 8b causes the piston 6 to slide inside the through-hole 32. In addition, as the piston 6 slides, the plunger 7 presses the injection solution ML and, as a result, the injection solution ML is ejected to the injection target region from the nozzle section 9. In the ejection completion state where ejection of the injection solution ML has been completed, while the pressing bottom section 8b is in contact with the end surface of the first end section 6a of the piston 6 as shown in the lower half of FIG. 3, since the plunger 7 abuts an inner wall surface of the nozzle holder 10 on which the nozzle section 9 is formed, sliding of the piston 6 is restricted. The position of the pressing bottom section 8b in this state is considered an ejection position and is represented by X2, and the position of the plunger 7 is represented by P2.

In this manner, in the injector 1, during the process of combustion of the gunpowder 22, the pressing bottom section 8b of the extending case 8 is to move from the start position X1 in the state prior to combustion to the ejection position X2 in the ejection completion state. A distance of movement (X2−X1) of the pressing bottom section 8b corresponds to a distance of movement (P2−P1) of the plunger 7 for ejecting the injection solution ML. In addition, in the process of the movement, in the extending case 8, the bellows section 8c is extended and the pressing bottom section 8b moves while the combustion product generated by combustion of the gunpowder 22 and the prescribed gas generated by combustion of the gas generating agent 40 are kept encapsulated in the combustion chamber 34, and the combustion product remains encapsulated in the combustion chamber 34 even in the ejection completion state. By having the extending case 8 continuously encapsulate the combustion product in this manner, an effect of the combustion product and the like on the injection solution ML can be suppressed. Furthermore, in the injector 1, since combustion pressure generated by the combustion of the gunpowder 22 and the combustion of the gas generating agent 40 mainly vibrates the extending case 8, the injector main body 2 is less likely to be vibrated and vibration and noise from the injector main body 2 are reduced.

In addition, the extending case 8 is configured so as to have a prescribed gap ΔD with respect to an inner wall surface 31a which defines the space 31 inside the injector main body 2 and which is in a vicinity of an end section of the through-hole 32 even in the ejection completion state or, in other words, in a state where the extending case 8 is extended to the maximum. It should be noted that, in FIG. 3, a position of the inner wall surface 31a is represented by X3 and the prescribed gap ΔD is present between the position X2 of the pressing bottom section 8b and the position X3 of the inner wall surface 31a in the ejection completion state. In other words, a distance in the axial direction of the through-hole 32 between the pressing bottom section 8b and the surface 31a which is a surface opposing the pressing bottom section 8b in the inner wall surface described earlier in the state prior to combustion is set larger than the distance of movement (X2−X1) by the pressing bottom section 8b. As a result, since the extending case 8 no longer collides with the inner wall surface 31a, the extending case 8 is less likely to be damaged and the combustion product and the like can be encapsulated in a preferable manner. In addition, since vibration imparted to the injector main body 2 due to the extending case 8 colliding with the inner wall surface 31a is suppressed, vibration and noise from the injector main body 2 are reduced.

As described above, the injector 1 according to the present embodiment suppresses effects of a combustion product and a prescribed gas on the injection solution ML and, at the same time, enables the injection solution ML to be preferably pressurized.

Modifications

Figure 4:
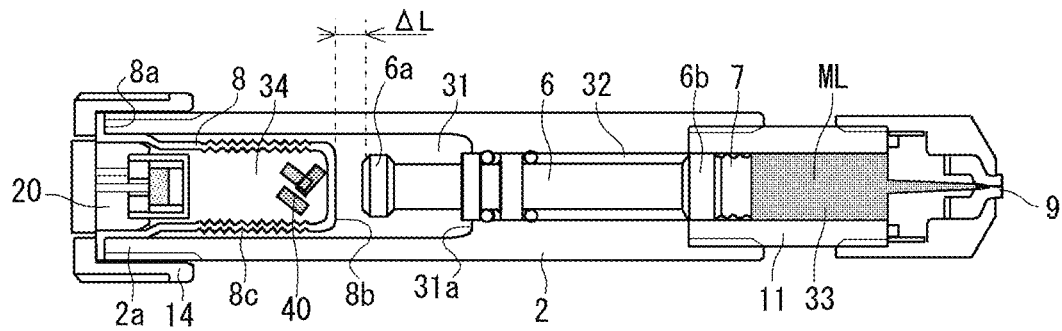
FIG. 4 is a diagram showing a schematic configuration of a modification of the injector shown in FIGS. 1A-1C.

While the extending case 8 is arranged inside the injector main body 2 in a state where the pressing bottom section 8b is in contact with the first end section 6a of the piston 6 in the state prior to combustion in the embodiment described above, in an alternative aspect, the extending case 8 may be arranged inside the injector main body 2 in a state where the pressing bottom section 8b is separated from the first end section 6a of the piston 6 in the state prior to combustion as shown in FIG. 4. In the configuration shown in FIG. 4, a distance of separation between the pressing bottom section 8b and the first end section 6a in the state prior to combustion is represented by ΔL. Even in a mode in which the distance of separation ΔL is secured as described above, the extension of the bellows section 8c due to a pressure rise inside the combustion chamber 34 causes the pressing bottom section 8b to come into contact with the first end section 6a and the piston 6 is to be subsequently pressed. Even in such a case, when the extending case 8 is extended to the maximum, the pressing bottom section 8b favorably does not come into contact with the inner wall surface 31a.

In addition, while the gas generating agent 40 is stored in the combustion chamber 34 in the embodiment described above, even in an alternative aspect in which the gas generating agent 40 is not stored in the combustion chamber 34, since the pressure rise inside the space 29 is not inhibited by an expansion of capacity of the space in which gunpowder combustion takes place until the cup 21 is breached, the pressure inside the initiator 20 promptly rises to prescribed pressure. As a result, combustion energy of the gunpowder 22 can be effectively generated, the combustion energy can be promptly transferred to the piston 6, and pressurization of the injection solution ML can be performed in a preferable manner. Furthermore, at the same time, since the combustion product continues to be encapsulated by the extending case 8, an effect of the combustion product on the injection solution ML and combustion noise can be suppressed.

Second Embodiment

Figure 5:
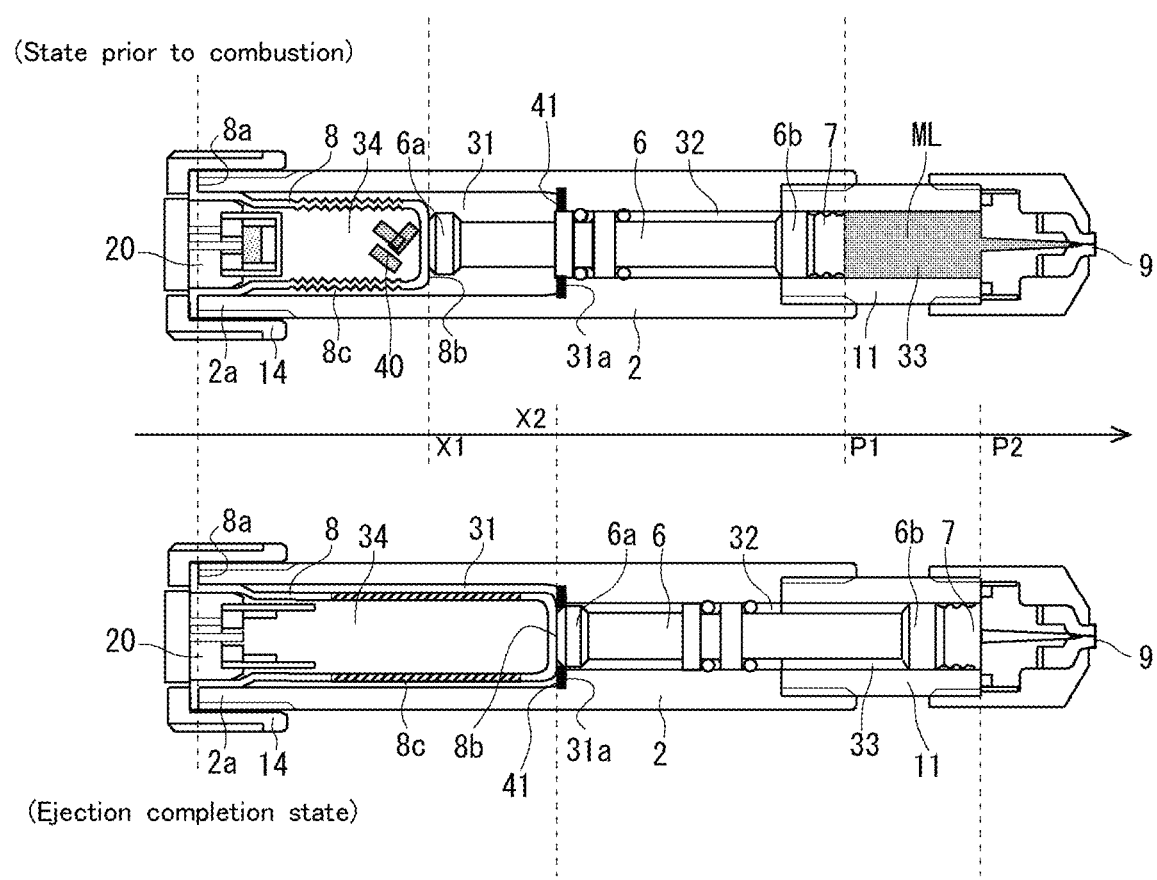
FIG. 5 is a diagram showing a comparison between a state prior to gunpowder combustion and a state after combustion (an ejection completion state) in an initiator in an injector according to a second embodiment of the present invention.

Next, a second embodiment of the injector 1 will be described with reference to FIG. 5. In FIG. 5, an upper half shows a configuration of the injector 1 in a state prior to ignition and a lower half shows a configuration of the injector 1 in the ejection completion state in a similar manner to FIG. 3. The comparative representation of both states is similar to FIG. 3. In the injector 1 according to the present embodiment, a cushioning member 41 formed by an elastic material is installed on the inner wall surface 31a of the space 31.

When combustion of the gunpowder 22 in the initiator 20 and combustion of the gas generating agent 40 occur, the bellows section 8c is extended. Accordingly, the pressing bottom section 8b presses the piston 6 via the first end section 6a. When the bellows section 8c becomes fully extended or before the bellows section 8c is fully extended, the pressing bottom section 8b comes into contact with the inner wall surface 31a via the cushioning member 41 to inhibit the extension of the bellows section 8c. Accordingly, a pressing action on the piston 6 via the extending case 8 is to be stopped. Even in this configuration, effects of a combustion product and a prescribed gas on the injection solution ML can be suppressed and, at the same time, the injection solution ML can be preferably pressurized. Furthermore, since the pressing bottom section 8b is capable of reducing, by coming into contact with the cushioning member 41, an impact received from the side of the inner wall surface 31a during the contact, the extending case 8 is less likely to be damaged, a preferable encapsulation of the combustion product and the like can be realized, and since vibration imparted to the injector main body 2 by the impact is suppressed, vibration and noise from the injector main body 2 are reduced.

Third Embodiment

A third embodiment of the injector 1 will now be described. As described above, in the injector 1 according to embodiments of the present invention, the piston 6 is pressed as the extending case 8 extends. Therefore, in order to maintain an encapsulated state of the combustion product of the gunpowder 22 and the prescribed gas of the gas generating agent 40 in the combustion chamber 34 in a preferable manner, strength of the pressing bottom section 8b of the extending case 8 is favorably increased in consideration of the fact that transfer energy to the piston acts on the pressing bottom section 8b. In consideration thereof, a case thickness of the pressing bottom section 8b may be formed thicker than a case thickness of the non-extending section 8d in the side wall section of the extending case 8.

Figure 6:
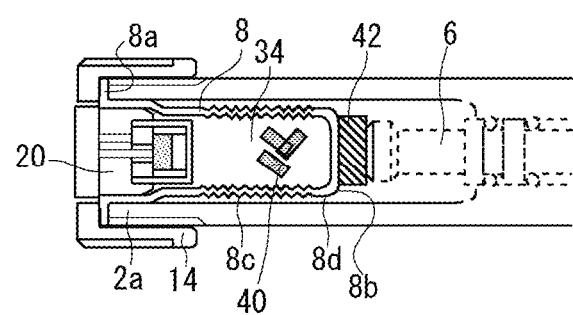
FIG. 6 is a diagram schematically showing a part of an injector according to a third embodiment of the present invention.

In addition, alternatively, as shown in FIG. 6, a reinforcing plate 42 having a prescribed thickness may be provided on an outer surface or an inner surface of the pressing bottom section 8b in order to increase the strength of the pressing bottom section 8b. The reinforcing plate 42 may be formed by a same material as the extending case 8 or by another material suitable for reinforcement. In addition, the prescribed thickness of the reinforcing plate 42 is set to a thickness which imparts strength to the reinforcing plate 42 so that a breach of the extending case 8 can be suppressed.

Other Embodiments

With the injector 1 according to embodiments of the present invention, in addition to cases where the injection solution described above is injected into a skin structure, for example, in the field of regenerative medicine with respect to humans, cultured cells, stem cells, and the like can be seeded to cells or scaffold tissue/scaffolds to be used as injection targets. For example, as described in Japanese Patent Application Laid-open No. 2008-206477, cells which can be appropriately determined by a person skilled in the art in accordance with a site of implantation and a purpose of recellularization such as endothelial cells, endothelial progenitor cells, bone marrow cells, preosteoblasts, chondrocytes, fibroblasts, skin cells, muscle cells, liver cells, kidney cells, intestinal cells, stem cells, and any other cells considered in the field of regenerative medicine can be injected by the injector 1. More specifically, prescribed cells are injected and transplanted into a region of transplantation by storing a liquid containing cells to be seeded (a cellular suspension) in the storage chamber 33 and pressurizing the liquid.

In addition, the injector 1 according to embodiments of the present invention can also be used to deliver DNA or the like to cells, scaffold tissue/scaffolds, and the like such as described in Japanese Translation of PCT Application No. 2007-525192. In this case, since the use of the injector 1 according to embodiments of the present invention enables an effect on the cells, scaffold tissue/scaffolds, and the like to be suppressed as compared to delivery using a needle, it can be said that the use of the injector 1 according to embodiments of the present invention is more favorable.

Furthermore, the injector 1 according to embodiments of the present invention can also be used when directly delivering various genes, cancer suppressor cells, a lipid envelope, or the like to object tissue or when administering an antigen gene in order to improve immunity to pathogens. Moreover, the injector 1 can also be used in various fields of disease treatment (the fields described in Japanese Translation of PCT Application No. 2008-508881, Japanese Translation of PCT Application No. 2010-503616, and the like), the field of immunological medicine (the field described in Japanese Translation of PCT Application No. 2005-523679), and the like, and fields in which the injector 1 is usable are not intentionally limited.

What is claimed is:

1. An injector for injecting an injection objective substance into an injection target region, the injector comprising:
   an injector main body having a through-hole formed in an axial direction;
   a piston section arranged so as to be slidable inside the through-hole;
   a syringe section arranged on a tip side of the injector main body, the syringe section comprising a storage chamber configured to store the injection objective substance, a plunger configured to pressurize the injection objective substance inside the storage chamber as the piston section slides, and a nozzle section including a flow path through which the injection objective substance that is present inside the storage chamber and has been pressurized by the plunger flows, the nozzle configured to eject the injection objective substance from an ejection port formed at a tip of the flow path;
   an ignition device comprising a partition member which forms a first space to store a gunpowder and which is formed of a prescribed rigid material such that the partition member is breached based on a rise in pressure of the first space when the gunpowder is burned; and
   a case including a base section fixed on a side of the ignition device, the case arranged in a space inside the injector main body so as to cover the ignition device, the case defining a second space with the partition member of the ignition device and encapsulating, inside the second space, a combustion product generated by combustion of the gunpowder in the ignition device, wherein the case includes:
an extending section configured to, based on a rise in pressure inside the second space by gunpowder combustion in the ignition device, extend in an approach direction in which a part of the case approaches a prescribed end section of the piston on a side opposite to an end section opposing the plunger; and
a pressing section provided in the part of the case and configured to press the prescribed end section of the piston as the extending section extends,
the injector further comprising a cushioning member provided on a prescribed inner wall surface which forms an internal space of the injector main body, the inner wall surface being in a vicinity of an end surface of the through-hole and opposing the part of the case, and when the extending section is extended by gun owder combustion in the inition device, the extending section comes into contact with the cushioning member and the extension of the extending section is stopped.

2. The injector according to claim 1, further comprising a gas generating agent stored inside the second space and configured to generate a prescribed gas by combustion, and
wherein the extending section is configured such that the part of the case extends in the approach direction as pressure inside the second space rises in response to gunpowder combustion in the ignition device and combustion of the gas generating agent.

3. The injector according to claim 1, wherein the extending section is formed in a side wall section of the case opposing an inner wall surface that extends in an axial direction of the injector main body so as to be folded in a bellows shape in a state prior to gunpowder combustion in the ignition device, and wherein the extending section is configured so as to extend in the axial direction in response to gunpowder combustion in the ignition device.

4. The injector according to claim 1, wherein the part of the case is an end surface on a tip side of the case, and wherein an area of the tip-side end surface of the case is formed larger than an end surface area of the prescribed end section of the piston section.

5. The injector according to claim 1, wherein the part of the case is thicker than the remaining portions of the case.

6. The injector according to claim 1, wherein a reinforcing plate having a prescribed thickness is provided inside or outside the case in the part of the case.

7. The injector according to claim 1, wherein the case is arranged inside the injector main body so that the pressing section comes into contact with the prescribed end section of the piston section in a state prior to gunpowder combustion in the ignition device.

8. An injector for injecting an injection objective substance into an injection target region, the injector comprising:
an injector main body having a through-hole formed in an axial direction;
a piston section arranged so as to be slidable inside the through-hole;
a syringe section arranged on a tip side of the injector main body, the syringe section comprising a storage chamber configured to store the injection objective substance, a plunger configured to pressurize the injection objective substance inside the storage chamber as the piston section slides, and a nozzle section including a flow path through which the injection objective substance that is present inside the storage chamber and has been pressurized by the plunger flows, the nozzle configured to eject the injection objective substance from an ejection port formed at a tip of the flow path;
an ignition device comprising a partition member which forms a first space to store a gunpowder and which is formed of a prescribed rigid material such that the partition member is breached based on a rise in pressure of the first space when the gunpowder is burned; and
a case including a base section fixed on a side of the ignition device, the case arranged in a space inside the injector main body so as to cover the ignition device, the case defining a second space with the partition member of the ignition device and encapsulating, inside the second space, a combustion product generated by combustion of the gunpowder in the ignition device,
wherein the case includes:
an extending section configured to, based on a rise in pressure inside the second space by gunpowder combustion in the ignition device, extend in an approach direction in which a part of the case approaches a prescribed end section of the piston on a side opposite to an end section opposing the plunger, and
a pressing section provided in the part of the case and configured to press the prescribed end section of the piston as the extending section extends, and
wherein the injector is configured such that, in a state where the extending section is extended to the maximum in response to gunpowder combustion in the ignition device, a prescribed gap is present between the pressing section of the part of the case and a prescribed inner wall surface opposing the pressing section and forming an internal space of the injector main body, the inner wall surface being in a vicinity of an end section of the through-hole and opposing the part of the case.

9. The injector according to claim 8, wherein the pressing section of the part of the case is larger in width than that of the prescribed end section of the piston.

10. The injector according to claim 8, wherein the internal space of the injector main body is larger in width than that of the prescribed end section of the piston.

11. The injector according to claim 8, wherein the internal space of the injector main body houses the case such that a sidewall section of the case does not contact an inner wall of the internal space of the injector main body facing the sidewall section of the case.

12. The injector according to claim 11, wherein an inner wall of the injector main body does not contact an outer wall of the internal space facing the inner wall of the injector main body.

* * * * *